(12) United States Patent
Wakamiya

(10) Patent No.: US 9,304,140 B2
(45) Date of Patent: Apr. 5, 2016

(54) SAMPLE ANALYZER

(75) Inventor: Yuji Wakamiya, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/251,501

(22) Filed: Oct. 3, 2011

(65) Prior Publication Data

US 2012/0087830 A1    Apr. 12, 2012

(30) Foreign Application Priority Data

Oct. 12, 2010    (JP) .................................. 2010-229947

(51) Int. Cl.
*G01N 35/02*    (2006.01)
*G01N 35/00*    (2006.01)

(52) U.S. Cl.
CPC .......... *G01N 35/025* (2013.01); *G01N 35/0092* (2013.01)

(58) Field of Classification Search
CPC .................... G01N 35/025; G01N 35/0092
See application file for complete search history.

(56) References Cited

U.S. PATENT DOCUMENTS

| | | | |
|---|---|---|---|
| 5,988,857 A * | 11/1999 | Ozawa et al. ................ | 700/213 |
| 2005/0129576 A1 * | 6/2005 | Oonuma ........................ | 422/64 |
| 2007/0172390 A1 | 7/2007 | Ootani et al. | |
| 2009/0081794 A1 * | 3/2009 | Wakamiya et al. ............ | 436/43 |
| 2009/0191094 A1 * | 7/2009 | Kayahara et al. .............. | 422/64 |
| 2009/0196793 A1 * | 8/2009 | Omuro et al. ................. | 422/64 |
| 2009/0215183 A1 * | 8/2009 | Takehara et al. .............. | 436/47 |
| 2009/0292492 A1 * | 11/2009 | Nishida et al. ................ | 702/85 |

FOREIGN PATENT DOCUMENTS

| | | |
|---|---|---|
| EP | 0 867 724 A2 | 9/1998 |
| JP | 03-183955 A | 8/1991 |

* cited by examiner

*Primary Examiner* — Jill Warden
*Assistant Examiner* — Matthew Krcha
(74) *Attorney, Agent, or Firm* — Brinks Gilson & Lione

(57) ABSTRACT

A sample analyzer comprising: a sample dispenser for dispensing a sample into a reaction container; a sample transporter for sequentially transports a plurality of reaction containers along a transporting path; a processing station including a plurality of processing sections and a transferring section that transfers a reaction container between the sample transporter and the processing sections; and a controller is disclosed. The sample dispenser sequentially dispenses samples at intervals. The controller alternates the interval when problem occurred at any of the processing sections.

15 Claims, 10 Drawing Sheets

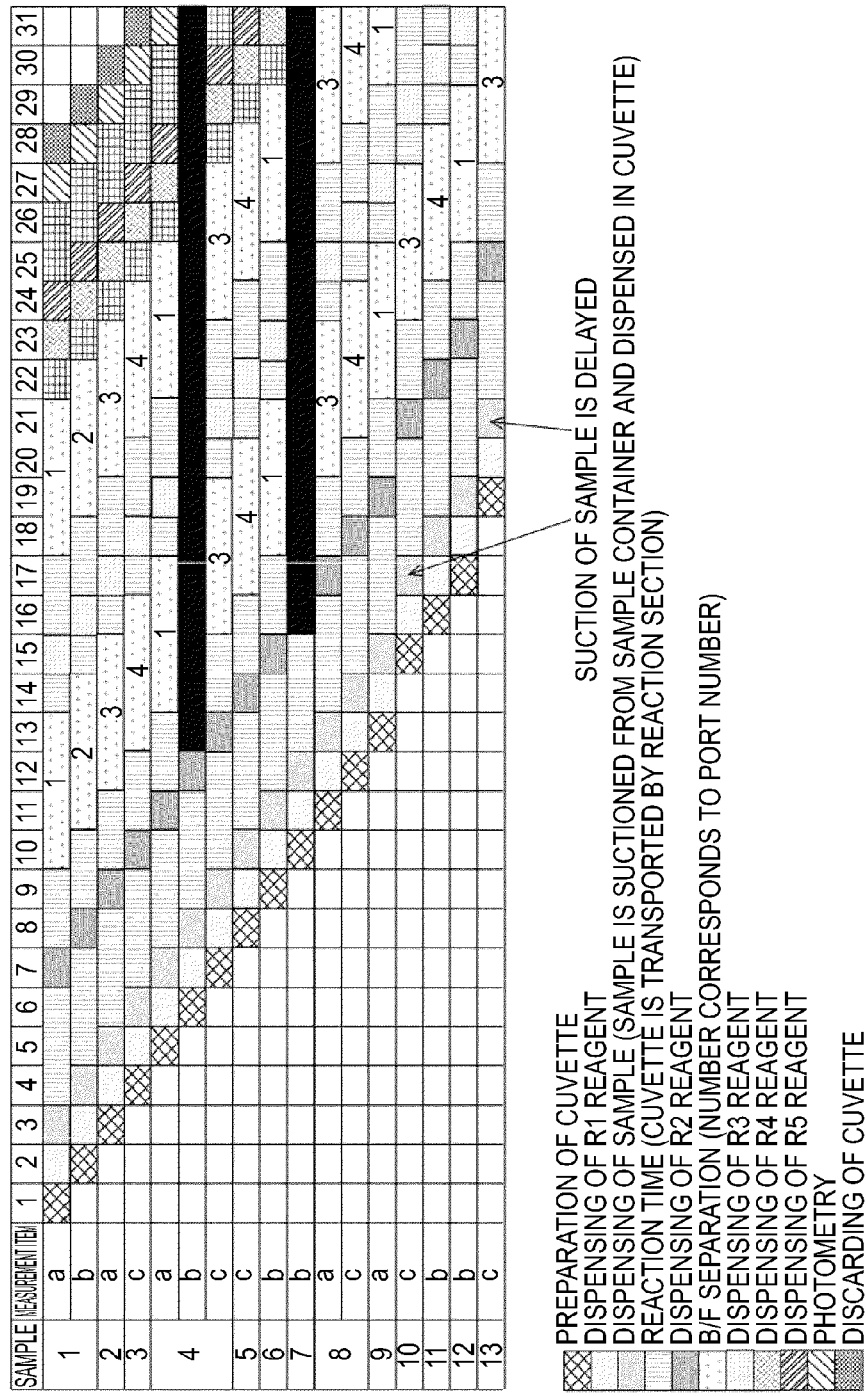

SAMPLE ANALYZER

RELATED APPLICATIONS

This application claims priority under 35 U.S.C. §119 to Japanese Patent Application No. 2010-229947 filed on Oct. 12, 2010, the entire content of which is hereby incorporated by reference.

BACKGROUND OF THE INVENTION

1. Field of the Invention

The present invention relates to a sample analyzer which automatically analyzes a sample such as blood or urine.

2. Description of the Related Art

In the past, there have been known sample analyzers such as immunoassay apparatuses, biochemical analyzers, blood cell counters, blood coagulation measuring apparatuses, in-urine physical component analyzers and urine qualitative analyzers.

An automatic analyzer disclosed in JP laid-open patent application publication H03-183955 is provided with a reaction table which includes a plurality of reaction containers containing specimens (samples) and reagents and is rotated with a predetermined rotation characteristic by a rotation driving section, a specimen dispenser which dispenses a specimen in a reaction container, a reagent dispenser which dispenses a reagent in a reaction container in which a specimen has been dispensed, a stirring section which stirs a specimen and a reagent in a reaction container, a photometric section which measures the concentration of a specimen in a reaction container, and a controller which controls operations of the sections.

The automatic analyzer disclosed in H03-183955 is configured as follows. The controller detects a problem and determines which one of the specimen dispenser, the reagent dispenser, and the stirring section relates to the content of the problem. When it is determined that the content of the problem relates to any of the above-described sections, mechanisms other than the reaction table and the section relating to the photometry are stopped, and the operations of the reaction table and the photometric section are continued. Therefore, when a problem occurs, a specimen which has already been stirred is subjected to the photometry and data thereof is obtained.

However, in the automatic analyzer disclosed in the above-described Patent Document 1, when a problem occurs in a part of the apparatus, it is impossible to newly dispense and process a sample continuously.

SUMMARY OF THE INVENTION

A first aspect of the present invention is A sample analyzer comprising: a sample dispenser for dispensing a sample into a reaction container; a sample transporter for sequentially transports a plurality of reaction containers along a transporting path; a processing station including a plurality of processing sections and a transferring section that transfers a reaction container between the sample transporter and the processing sections; and a controller for executing a sample processing operation for a sample, the sample processing operation including: (i) dispensing, by the sample dispenser, the sample into a reaction container; (ii) transporting, by the sample transporter, the dispensed reaction container along the transporting path; (iii) transferring, by the transferring section, the transported reaction container from the sample transporter to any of the processing sections; (iv) carrying out, by the processing section, a process on the sample in the reaction container; and (v) transferring, by the transferring section, the reaction container from the processing section to the sample transporter after completing the process, wherein the controller sequentially initiates the sample processing operations for a plurality of samples at predetermined intervals while continuing the sample processing operation for the other sample, when the controller determines that a problem occurs at any of the processing sections, the controller alternates the interval to continue the sample processing operation by using the processing section other than the processing section where the problem occurred.

BRIEF DESCRIPTION OF THE DRAWINGS

FIG. 11 is a timing chart partially showing another example of the sample measurement schedule.

DETAILED DESCRIPTION OF THE PREFERRED EMBODIMENTS

Hereinafter, preferred embodiments of the invention will be described with reference to the drawings.

[Configuration of Sample Analyzer]

Figure 1:
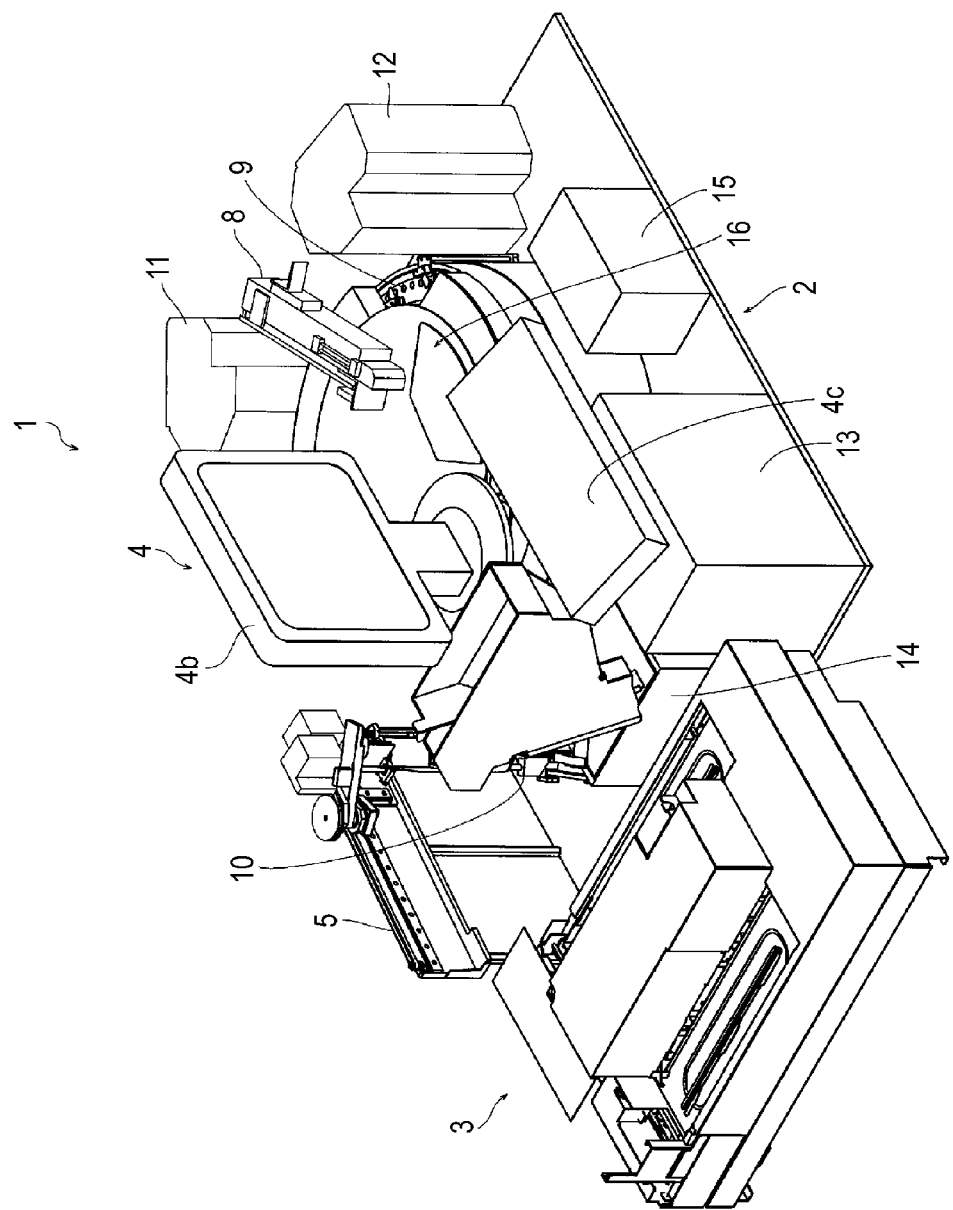
FIG. 1 is a perspective view showing the configuration of a sample analyzer according to an embodiment.
Figure 2:
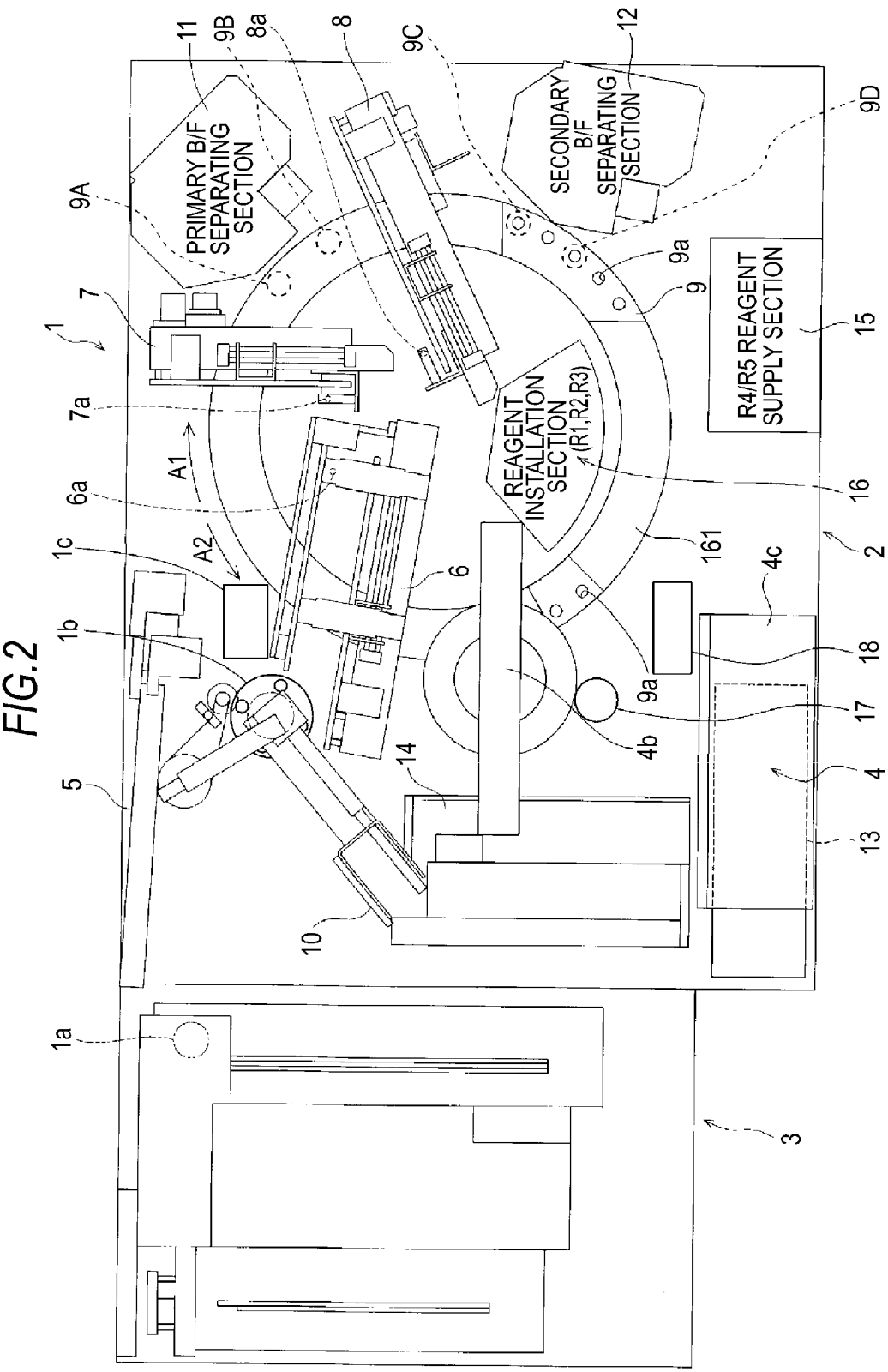
FIG. 2 is a plan view showing the configuration of the sample analyzer according to the embodiment.

FIG. 1 is a perspective view showing the configuration of a sample analyzer according this embodiment, and FIG. 2 is a plan view of the sample analyzer. A sample analyzer 1 according to this embodiment is an immunoassay apparatus for examining various items such as hepatitis B, hepatitis C, a tumor marker and a thyroid hormone using a sample such as blood. In this sample analyzer 1, a sample such as blood which is a measurement target and a buffer solution (R1 reagent) are mixed, and to this mixed liquid, magnetic particles (R2 reagent) are added which carry a capture antibody which is able to be bound to an antigen included in the sample. The capture antibody and the antigen are bound to each other, and then the magnetic particles are drawn to a magnet (not shown) of a primary B/F (bound free) separating section 11 (see FIGS. 1 and 2) to remove the free antigen. In addition, a labeled antibody (R3 reagent) is added, and the antigen to which the magnetic particles are bound and the labeled antibody are bound to each other. Then, the bound magnetic particles are drawn to a magnet (not shown) of a secondary B/F separating section 12 to remove the free labeled antibody. Furthermore, a dispersion liquid (R4 reagent) and a luminescent substrate (R5 reagent) which emits light in the course of the reaction with the labeled antibody are added, and then the amount of luminescence caused by the reaction of the labeled antibody and the luminescent substrate is measured. Through such a process, the antigen included in the sample which is bound to the labeled antibody is quantitatively measured.

As shown in FIGS. 1 and 2, this sample analyzer 1 is provided with a measuring unit 2, a sample transport unit (sampler) 3 which is disposed adjacent to the measuring unit 2, and an information processing unit 4 which is formed of a personal computer (PC) electrically connected to the measuring unit 2.

Figure 3:
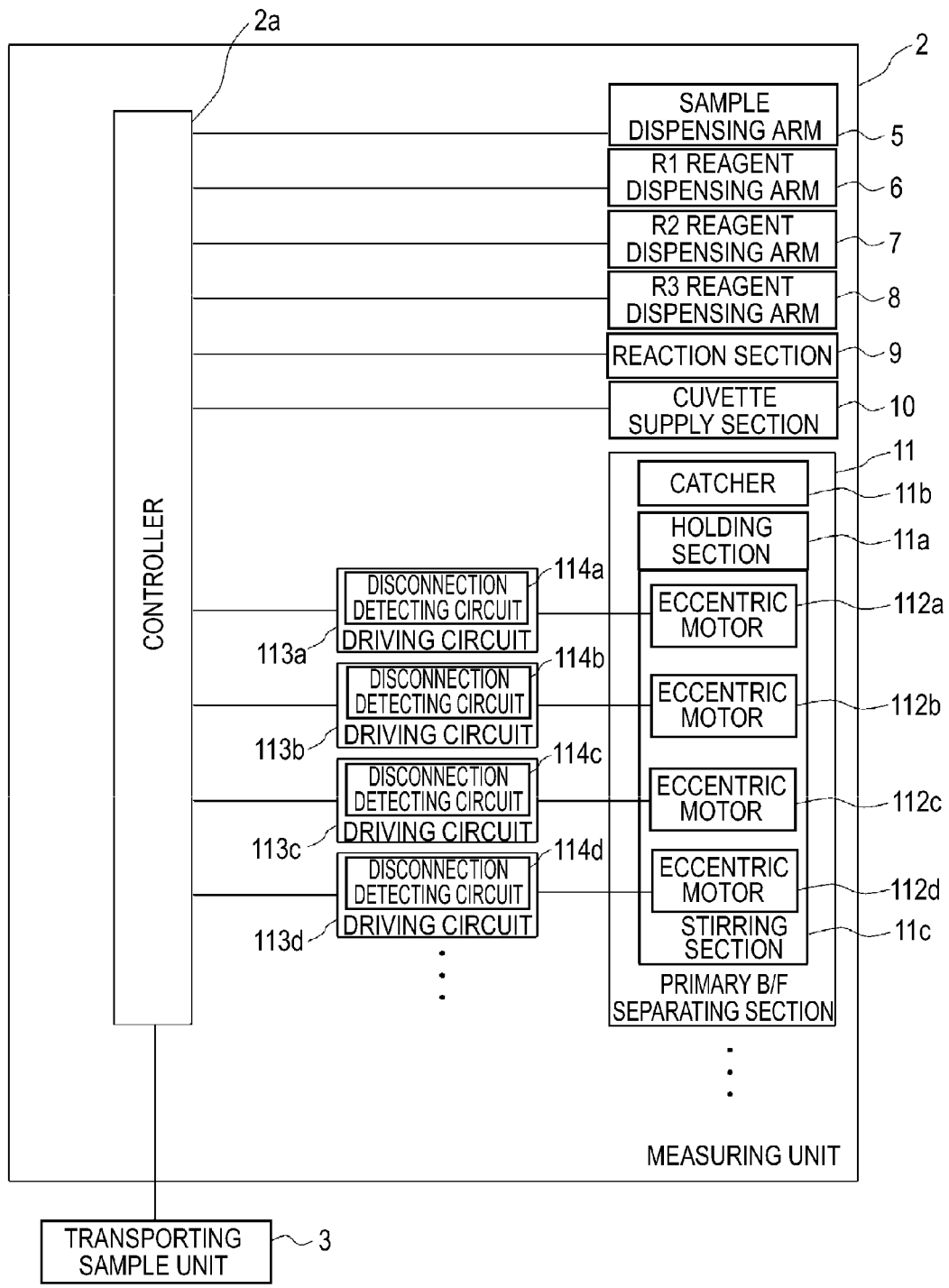
FIG. 3 is a block diagram showing a part of the configuration of a measuring unit.

FIG. 3 is a block diagram showing a part of the configuration of the measuring unit 2. The measuring unit 2 is configured to have a sample dispensing arm 5, an R1 reagent dispensing arm 6, an R2 reagent dispensing arm 7, an R3 reagent dispensing arm 8, a reaction section 9, a cuvette supply section 10, the primary B/F separating section 11, the secondary B/F separating section 12, a pipette tip supply section 13, a detecting section 14, an R4/R5 reagent supply section 15, a reagent installation section 16, a discarding section 17, and a catcher 18. In addition, as shown in FIG. 3, the mechanisms (various dispensing arms, reaction section 9, reagent installation section 16 and the like) in the measuring unit 2 are controlled by a controller 2a provided in the measuring unit 2. In addition, the sample transport unit 3 is also configured to be controlled by the controller 2a.

Figure 4:
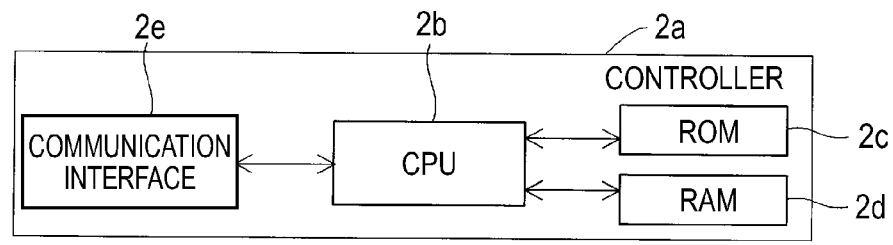
FIG. 4 is a block diagram showing the configuration of a controller of the measuring unit.

FIG. 4 is a block diagram showing the configuration of the controller 2a of the measuring unit 2. As shown in FIG. 4, the controller 2a is configured to mainly have a CPU 2b, a ROM 2c, a RAM 2d, and a communication interface 2e. The CPU 2b can execute a computer program which is stored in the ROM 2c and a computer program which is read out to the RAM 2d. The ROM 2c stores a computer program to be executed in the CPU 2b, data which is used in the execution of the computer program, and the like. The RAM 2d is used in the readout of a computer program which is stored in the ROM 2c. In addition, the RAM 2d is used as a work area of the CPU 2b when these computer programs are executed. The communication interface 2e is connected to the information processing unit 4 and has a function of transmitting optical information (data of the amount of luminescence caused by the reaction of the labeled antibody and the luminescent substrate) of a sample to the information processing unit 4 and receiving a signal from a controller of the information processing unit 4. In addition, the communication interface 2e has a function of transmitting a command from the CPU 2b to drive the sections of the sample transport unit 3 and the measuring unit 2.

The sample transport unit 3 is configured to be able to transport a rack in which a plurality of test tubes containing a sample is placed. In addition, the sample transport unit 3 is configured to transport a test tube containing a sample to a position 1a (see FIG. 2) at which the sample is suctioned by the sample dispensing arm 5.

The information processing unit 4 is formed of a computer which is configured to mainly have the controller (not shown) provided with a CPU, a ROM, a RAM, a hard disk and the like, a display section 4b, and a keyboard 4c. The information processing unit 4 receives from a user an input of a measurement order, a measurement start instruction, a reagent replacement instruction and the like, and outputs an operation instruction to the measuring unit 2 and the sample transport unit 3 in accordance with the input. In addition, the information processing unit 4 has a function of analyzing measurement data which is obtained by measuring a sample by the measuring unit 2 to obtain a sample analysis result and outputting the analysis result to the display section 4b.

Hereinafter, the configuration of the measuring unit 2 will be described in detail.

The cuvette supply section 10 is configured to be able to store a plurality of cuvettes and has a function of sequentially supplying the cuvettes one by one to a table 1b in which a sample is dispensed by the sample dispensing arm 5. In the measuring unit 2, the mechanisms repeat the same operation for each of continuous turns which are divided at predetermined time intervals (for example, 9 seconds) to perform the sample measurement. The above-described cuvette supply section 10 also supplies one cuvette in one turn, and this is continuously performed to sequentially supply cuvettes one by one. The sample dispensing table 1b has a plurality of annular holes in which a cuvette can be held. The sample dispensing table 1b receives a supplied cuvette at a cuvette receiving position. The sample dispensing table 1b is rotated by a predetermined angle in a counterclockwise direction, and thus an empty cuvette received at the cuvette receiving position is transferred to a position at which a reagent is dispensed by the R1 reagent dispensing arm 6 and transferred to a position at which a sample dispensed by the sample dispensing arm 5. The rotation of this sample dispensing table 1b by a predetermined angle is performed once in one turn. Accordingly, on the sample dispensing table 1b, receiving a cuvette (provision of cuvette), dispensing an R1 reagent in an empty reaction container, and dispensing a sample in the reaction container containing the R1 reagent dispensed therein are simultaneously performed in parallel.

The R1 reagent dispensing arm 6 is configured to suction an R1 reagent installed in the reagent installation section 16 and dispense (emit) the suctioned R1 reagent in a cuvette placed in the sample dispensing table 1b. In addition, a pipette 6a for suctioning and emitting an R1 reagent is attached to the R1 reagent dispensing arm 6 as shown in FIG. 2. Such an R1 reagent dispensing arm 6 performs the suction of an R1 reagent and the dispensing in a cuvette once in one turn.

The pipette tip supply section 13 has a function of transporting a plurality of entering pipette tips (not shown) one by one to a position at which a tip is mounted by the sample dispensing arm 5. A pipette tip is attached to a pipette tip end of the sample dispensing arm 5 at the tip mounting position. Such a pipette tip supply section 13 supplies one pipette tip in one turn.

The sample dispensing arm 5 has a function of suctioning a sample in a test tube which is transported to the sample suction position 1a by the sample transport unit 3 after the mounting of a pipette tip at the tip mounting position, and dispensing (emitting) the sample in a cuvette in which an R1 reagent is dispensed by the R1 reagent dispensing arm 6 at the sample dispensing position. Such a sample dispensing arm 5 performs the suction of one sample and the dispensing in a cuvette in one turn. A catcher 1c for transferring a cuvette is provided adjacent to the sample dispensing position. The catcher 1c grips a cuvette in which a sample is dispensed on the sample dispensing table 1b, takes the cuvette from a hole of the sample dispensing table 1b, and inserts the cuvette in a hole (cuvette installation section 9a) of the reaction section 9. In this manner, the cuvette in which the sample is dispensed is transferred to the reaction section 9 from the sample dispensing table 1b by the catcher 1c.

The R2 reagent dispensing arm 7 has a function of suctioning an R2 reagent installed in the reagent installation section 16. In addition, the R2 reagent dispensing arm 7 is configured to dispense (emit) the suctioned R2 reagent in a cuvette containing an R1 reagent and a sample. In addition, a pipette 7a for suctioning and emitting an R2 reagent is attached to the R2 reagent dispensing arm 7 as shown in FIG. 2. Such an R2 reagent dispensing arm 7 performs the suction of an R2 reagent and the dispensing in a cuvette once in one turn.

As shown in FIGS. 1 and 2, the reaction section 9 is formed in a hollow circular shape so as to surround the reagent installation section 16 having a circular shape in plan view. In addition, the reaction section 9 has a plurality of cuvette installation sections 9*a* which are disposed at predetermined intervals along the external form, and the cuvette installation sections 9*a* are formed in a concave shape in the circular shape so that a cuvette can be inserted therethrough. In addition, the reaction section 9 has a function of heating a cuvette set in a cuvette installation section 9*a* to about 42° C. That is, the reagent which is contained in the cuvette is heated to about 42° C. in the reaction section 9. Accordingly, the reaction of the sample and the various reagents in the cuvette is promoted. In addition, the reaction section 9 is configured to be rotatable in a clockwise direction (direction of the arrow A1) and has a function of moving a cuvette set in the cuvette installation section 9*a* to the respective processing positions at which various processes (dispensing of the reagent and the like) are performed. Such a reaction section 9 turns in the A1 direction by an angle between two adjacent cuvette installation sections 9*a* in one turn. Since this is continuously performed, the reaction section 9 turns intermittently.

Figure 5:
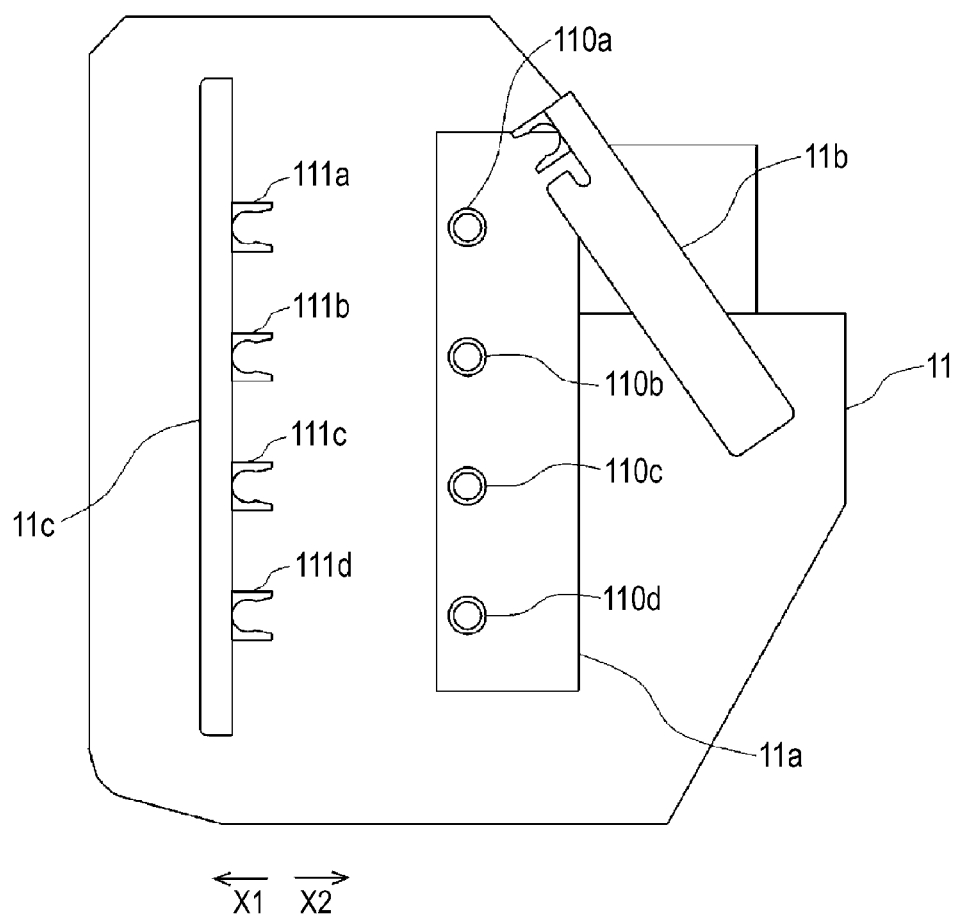
FIG. 5 is a plan view showing the schematic configuration of a primary B/F separating section.

The primary B/F separating section 11 is provided to separate (B/F separation) the free antigen and magnetic particles from the specimen in a cuvette. FIG. 5 is a plan view showing the schematic configuration of the primary B/F separating section 11. As shown in FIG. 5, the primary B/F separating section 11 is provided with a holding section 11*a* which holds a cuvette, a catcher 11*b* which grips and transfers a cuvette held in the reaction section 9 to the holding section 11*a*, and a stirring section 11*c* which stirs a cuvette. The holding section 11*a* is provided with four holding holes 110*a*, 110*b*, 110*c*, and 110*d* for holding a cuvette which are arranged in a row. The holding section 11*a* is configured to be horizontally movable in a direction (X1 and X2 directions in the drawing) perpendicular to the arrangement direction of the holding holes 110*a*, 110*b*, 110*c*, and 110*d* by a motor (not shown). In addition, the catcher 11*b* is configured to be oscillable in the horizontal direction and movable in the vertical direction. When a cuvette held in the reaction section 9 reaches a pickup position 9A, the catcher 11*b* grips and moves the cuvette upward to take the cuvette from the cuvette installation section 9*a* of the reaction section 9. Furthermore, the catcher 11*b* turns to transfer the gripped cuvette to a position above the empty one of the holding holes 110*a*, 110*b*, 110*c*, and 110*d*, and is moved downward to insert the cuvette in the holding hole. Thereafter, the catcher 11*b* turns in a direction separating from the cuvette and releases the engagement with the cuvette. In this manner, the cuvette is transferred to the holding section 11*a* from the reaction section 9.

The holding section 11*a* moves in the X1 direction while holding the cuvette. The stirring section 11*c* is provided on the side of the X1 direction of the holding section 11*a*. In the stirring section 11*c*, four stirring mechanisms 111*a*, 111*b*, 111*c*, and 111*d* are arranged in parallel. The respective stirring mechanisms 111*a*, 111*b*, 111*c*, and 111*d* are configured to be able to grip a cuvette by interposing the cuvette. The stirring mechanisms 111*a*, 111*b*, 111*c*, and 111*d* correspond to the holding holes 110*a*, 110*b*, 110*c*, and 110*d*, respectively, and by moving the holding section 11*a* in the X1 direction, a cuvette which is held in the holding hole 110*a* is gripped by the stirring mechanism 111*a*, a cuvette which is held in the holding hole 110*b* is gripped by the stirring mechanism 111*b*, a cuvette which is held in the holding hole 110*c* is gripped by the stirring mechanism 111*c*, and a cuvette which is held in the holding hole 110*d* is gripped by the stirring mechanism 111*d*. In addition, the stirring section 11*c* is movable in the vertical direction by the power of the motor (not shown). The stirring section 11*c* is moved upward in a state in which the stirring mechanisms 111*a*, 111*b*, 111*c*, and 111*d* grip the cuvettes which are stored in the holding holes 110*a*, 110*b*, 110*c*, and 110*d*, respectively, and thus the cuvettes are taken from the holding holes 110*a*, 110*b*, 110*c*, and 110*d*. The stirring mechanisms 111*a*, 111*b*, 111*c*, and 111*d* are provided with eccentric motors 112*a*, 112*b*, 112*c*, and 112*d*, respectively (see FIG. 3). The eccentric motors 112*a*, 112*b*, 112*c*, and 112*d* are driven in a state in which the cuvettes taken from the holding holes 110*a*, 110*b*, 110*c*, and 110*d* are gripped by the stirring mechanisms 111*a*, 111*b*, 11*c*, and 111*d*. Accordingly, the stirring mechanisms 111*a*, 111*b*, 111*c*, and 111*d* vibrate with the cuvettes, and the sample, the R1 reagent and the R2 reagent are stirred in the cuvette.

After the stirring of the liquids in the cuvettes, the stirring section 11*c* is moved downward and the cuvettes which are gripped by the stirring mechanisms 111*a*, 111*b*, 111*c*, and 111*d*, respectively, are inserted again in the holding holes 110*a*, 110*b*, 110*c*, and 110*d*. After the insertion of the cuvettes, the holding section 11*a* moves in the X2 direction to the position shown in FIG. 5.

In the state shown in FIG. 5, four pipettes which can move in the vertical direction are disposed above the holding holes 110*a*, 110*b*, 110*c*, and 110*d*, respectively (not shown). These four pipettes are moved downward to be inserted in the cuvettes which are held in the holding holes 110*a*, 110*b*, 110*c*, and 110*d*, respectively. Magnets (not shown) are attached to inner walls of the holding holes 110*a*, 110*b*, 110*c*, and 110*d*, respectively, to be disposed one by one on a side surface of each cuvette. The magnetic particles in each cuvette are suctioned (collection of magnetism) by the magnet and only the liquid in the cuvette is suctioned by the pipette. In addition, each pipette is configured to emit a cleaning liquid into the cuvette. The cleaning liquid enters the cuvette and then the holding section 11*a* moves again in the X1 direction. The cuvettes are lifted by the stirring mechanisms 111*a*, 111*b*, 111*c*, and 111*d*, the liquids and the magnetic particles in the cuvettes are stirred, and then the cuvettes are set in the holding section 11*a*. Again, the magnetic particles (and the antigen and the capture antibody bound to the magnetic particles) are collected and the liquids in the cuvettes are suctioned by the pipettes. The free antigen is removed from the cuvette by repeating such an operation plural times.

When the holding section 11*a* moves in the X2 direction, the cuvette (that is, the cuvette which is initially transferred to the holding section 11*a* from the reaction section 9 among the cuvettes held in the holding holes 110*a*, 110*b*, 110*c*, and 110*d*) in which a primary B/F separation process of removing the free antigen has ended is gripped by the catcher 11*b* and then lifted in that state to be taken from the holding hole. Furthermore, the catcher 11*b* turns to transport the gripped cuvette up to above the cuvette installation section 9*a* which is positioned at a return position 9B of the reaction section 9 and is moved downward to insert the cuvette in the cuvette installation section 9*a*. Then, the catcher 11*b* turns in a direction separating from the cuvette and releases the engagement with the cuvette. In this manner, the cuvette is transferred to the reaction section 9 from the holding section 11*a*.

Such a primary B/F separating section 11 executes the transfer of one cuvette to the holding section 11*a* from the reaction section 9 in one turn, the stirring of liquids and magnetic particles in the cuvettes held in the holding section 11*a*, the removal of the liquids in the cuvettes, and the transfer of one cuvette to the reaction section 9 from the holding section 11a. Each of the holding holes 110a, 110b, 110c, and 110d correspond to a port for stirring the liquid and the magnetic particles in the cuvette and removing the unnecessary component in the cuvette (primary B/F separation process). In greater detail, the holding hole 110a corresponds to a first port, the holding hole 110b corresponds to a second port, the holding hole 110c corresponds to a third port, and the holding hole 110d corresponds to a fourth port. In the creation of a schedule to be described later, a port is assigned for each cuvette, and in the assigned port, the primary B/F separation process is performed with regard to each cuvette. That is, new cuvettes are fed into the holding section 11a one by one in one turn, the stirring of the liquid and the magnetic particles and the suction of the liquid by the pipette are performed with respect to one cuvette in the primary B/F separating section 11 during total four turns, and the cuvettes are discharged one by one in one turn from the holding section 11a. In addition, a cuvette which is transported to the primary B/F separating section 11 is held in an assigned one of the holding holes (ports) 110a, 110b, 110c, and 110d, and is not moved to another holding hole (port) during the four turns in which the cuvette is installed in the primary B/F separating section 11. That is, one cuvette corresponds to one of the stirring mechanisms 111a, 111b, 111c, and 111d, and the liquid and the magnetic particles in the cuvette are stirred by the stirring mechanism during the four turns.

As shown in FIG. 3, each of the holding section 11a, the catcher 11b, and the stirring section 11c of the primary B/F separating section 11 is connected to the controller 2a and controlled by the controller 2a. In addition, the eccentric motors 112a, 112b, 112c, and 112d which are provided in the respective stirring mechanisms 111a, 111b, 111c, and 111d of the stirring section 11c are connected to the controller 2a via driving circuits 113a, 113b, 113c, and 113d, respectively. The driving circuits 113a, 113b, 113c, and 113d are provided with a switch (not shown) to switch the connection/disconnection between a constant-voltage power supply (not shown) and the eccentric motors 112a, 112b, 112c, and 112d. The controller 2a controls ON/OFF of the switches to switch the operation/stop of the eccentric motors 112a, 112b, 112c, and 112d. In addition, the driving circuits 113a, 113b, 113c, and 113d are provided with disconnection detecting circuits 114a, 114b, 114c, and 114d for detecting the disconnection of the eccentric motors 112a, 112b, 112c, and 112d, respectively. Each of these disconnection detecting circuits 114a, 114b, 114c, and 114d has a resistance for disconnection detection which is provided between the constant-voltage power supply and the eccentric motor, and the value of a current flowing to this resistance is output to the controller 2a. The controller 2a receives an output signal of each of the disconnection detecting circuits 114a, 114b, 114c, and 114d and compares the respective current values with a predetermined reference value. During the driving of the eccentric motors 112a, 112b, 112c, and 112d, a current equal to or greater than the reference value flows to the resistances for disconnection detection, but when disconnection occurs at any of the eccentric motors 112a, 112b, 112c, and 112d, no current flows to the resistance which is connected to the eccentric motor with the disconnection. The controller 2a determines that disconnection has occurred when a current value of the resistance for disconnection detection is less than the reference value.

The R3 reagent dispensing arm 8 has a function of suctioning an R3 reagent installed in the reagent installation section 16. In addition, the R3 reagent dispensing arm 8 is configured to, when a cuvette containing a specimen after the B/F separation by the primary B/F separating section 11 is transferred to the reaction section 9 from the primary B/F separating section 11, dispense (emit) a suctioned R3 reagent in the cuvette. In addition, as shown in FIG. 2, a pipette 8a for suctioning and emitting an R3 reagent is attached to the R3 reagent dispensing arm 8. Such an R3 reagent dispensing arm 8 performs the suction of an R3 reagent and the dispensing in a cuvette once in one turn.

The secondary B/F separating section 12 is configured to transfer a cuvette containing a reagent after the B/F separation by the primary B/F separating section 11 and an R3 reagent to the secondary B/F separating section 12 from the reaction section 9 by a catcher (not shown), and then to separate the free R3 reagent (unnecessary component) and the magnetic particles from the specimen in the cuvette. Since the configuration of this secondary B/F separating section 12 is the same as the configuration of the primary B/F separating section 11, a description thereof will be omitted.

The R4/R5 reagent supply section 15 is configured to sequentially dispense an R4 reagent and an R5 reagent in a cuvette containing a specimen after the B/F separation by the secondary B/F separating section 12 by a tube (not shown). Such an R4/R5 reagent supply section 15 dispenses an R4 reagent in one cuvette in one turn and dispenses an R5 reagent in the cuvette at next one turn.

The detecting section 14 is provided to measure the amount of an antigen included in a sample by acquiring the light which is generated during the course of the reaction of a luminescent substrate with a labeled antibody bound to the antigen of the sample which is subjected to a predetermined process by a photo multiplier tube. Such a detecting section 14 measures the amount of the antigen with respect to one sample in one turn.

The discarding section 17 is provided with a hole through which a cuvette subjected to the detection by the detecting section enters, and a discarding bag (not shown) containing an entering cuvette.

The catcher 18 picks up a cuvette which is positioned at a predetermined pickup position in the reaction section 9 and transfers the cuvette to the detecting section 14. Furthermore, the catcher 18 picks up a cuvette subjected to the detection by the detecting section and enters the cuvette to the discarding section 17.

[Operation of Sample Analyzer]

Next, the operation of the sample analyzer 1 according to this embodiment will be described.

<Procedures of Analysis for Each Sample>

First, the procedures of the sample analysis will be described. The procedures of the sample analysis of the sample analyzer 1 according to this embodiment do not differ depending on measurement items (hepatitis B, hepatitis C, tumor marker, thyroid hormone and the like) of a sample and all the analyses are performed in accordance with certain procedures.

Figure 6:
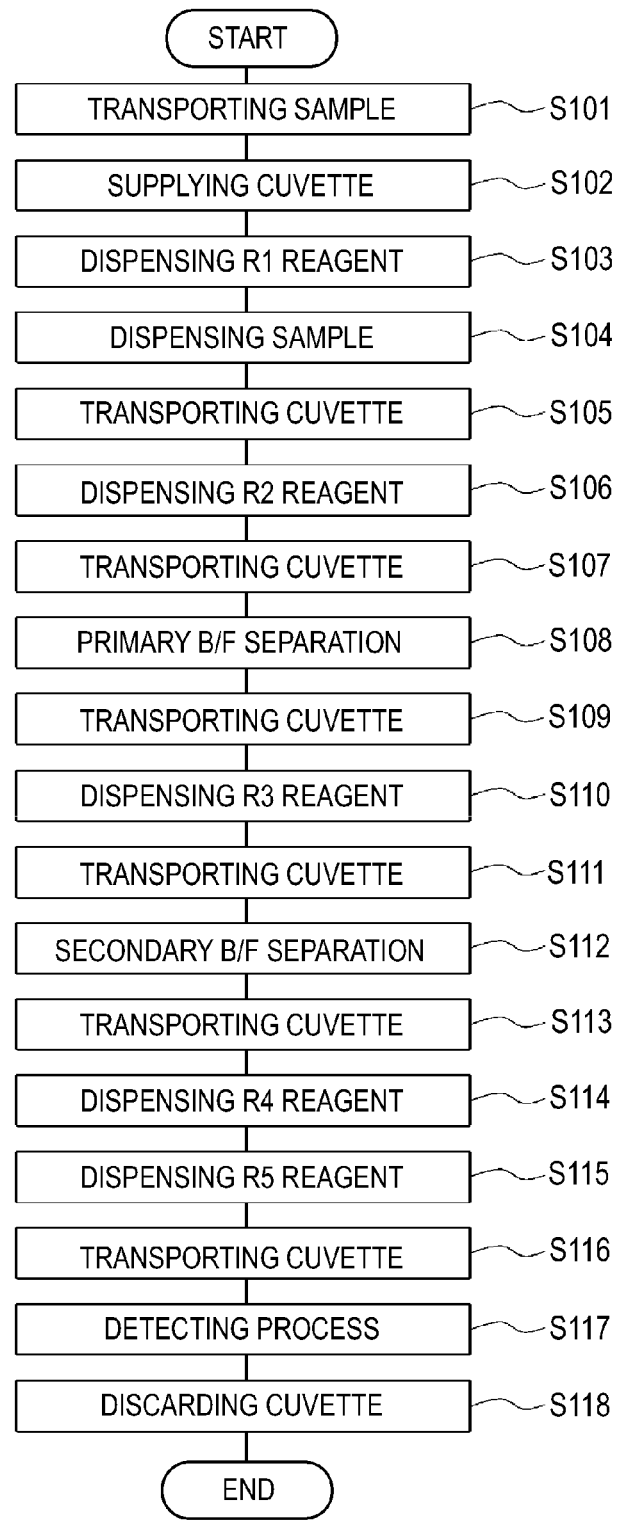
FIG. 6 is a flowchart showing the procedures of the sample analysis of the sample analyzer according to the embodiment.

FIG. 6 is a flowchart showing the procedures of the sample analysis of the sample analyzer according to this embodiment. First, by the sample transport unit 3, a rack in which a plurality of test tubes containing a sample is placed is transported and a test tube containing a sample is positioned at the sample suction position 1a (Step S101). In addition to this, one cuvette is supplied from the cuvette supply section 10 (Step S102). This cuvette is placed in the sample dispensing table 1b and is positioned at the R1 reagent dispensing position due to the rotation of the sample dispensing table 1b in a counterclockwise direction, and thus an R1 reagent is dispensed in the cuvette by the R1 reagent dispensing arm 6 (Step S103). Then, the sample dispensing table 1b rotates and the cuvette containing the R1 reagent dispensed therein is positioned at the sample dispensing position.

A pipette tip is supplied from the pipette tip supply section 13 and mounted on the sample dispensing arm 5. Then, the sample dispensing arm 5 suctions a sample from a test tube positioned at the sample suction position 1a and dispenses the sample in the cuvette positioned at the sample dispensing position (Step S104).

The cuvette in which the R1 reagent and the sample are dispensed is transferred to one cuvette installation section 9a of the reaction section 9 from the sample dispensing table 1b and is transported to an R2 reagent dispensing position due to the turning of the reaction section 9 in the A1 direction (Step S105). At this time, since the reaction section 9 turns by a predetermined angle in one turn, the cuvette reaches the R2 reagent dispensing position for a predetermined R1 reagent reaction time. When the cuvette reaches the R2 reagent dispensing position, an R2 reagent is dispensed in the cuvette by the R2 reagent dispensing arm 7 (Step S106). When the dispensing of the R2 reagent ends, the reaction section 9 further turns in the A1 direction, and thus the cuvette is transported to the above-described pickup position 9A (Step S107). The cuvette which reaches the pickup position 9A is transferred to the primary B/F separating section 11 by the catcher 11b, and the sample which is contained in the cuvette is subjected to the primary B/F separation (Step S108).

The cuvette in which the primary B/F separation has ended is transferred to the cuvette installation section 9a at the above-described return position 9B of the reaction section 9 by the catcher 11b, and is transported to an R3 reagent dispensing position due to the turning of the reaction section 9 in the A1 direction (Step S109). When the cuvette reaches the R3 reagent dispensing position, the R3 reagent dispensing arm 8 dispenses an R3 reagent in the cuvette (Step S110). When the dispensing of the R3 reagent ends, by the reaction section 9 further turning in the A1 direction, the cuvette is transported to a cuvette pickup position 9C for the secondary B/F separation (Step S111). The cuvette which reaches the pickup position 9C is transferred to the secondary B/F separating section 12 by the catcher of the secondary B/F separating section 12, and the sample which is contained in the cuvette is subjected to the secondary B/F separation (Step S112).

The cuvette in which the secondary B/F separation has ended is transferred to the cuvette installation section 9a at a predetermined return position 9D of the reaction section 9 by the catcher of the secondary B/F separating section 12. Then, the cuvette is transported to a cuvette pickup position for R4/R5 reagent supply due to the turning of the reaction section 9 in the A1 direction (Step S113). When the cuvette reaches the cuvette pickup position, the cuvette is transferred to the R4/R5 reagent supply section 15 by a catcher (not shown), an R4 reagent is dispensed therein (Step S114), and further an R5 reagent is dispensed therein (Step S115).

When the dispensing of the R4/R5 reagents ends, the cuvette is transferred to the cuvette installation section 9a at the predetermined position in the reaction section 9 from the R4/R5 reagent supply section 15, and due to the further turning of the reaction section 9 in the A1 direction, the cuvette is transported to a predetermined pickup position for a predetermined reaction time (Step S116). When the cuvette reaches the pickup position, the cuvette is picked up from the reaction section 9 by the catcher 18 and transferred to the detecting section 14. The amount of the antigen in the sample is measured by the detecting section 14 (Step S117). The measurement result is transmitted to the information processing unit 4 from the measuring unit 2, and the information processing unit 4 analyzes the measurement data to generate the sample analysis result. Such a sample analysis result is recorded on the hard disk of the information processing unit 4. When the detecting process ends, the catcher 18 picks up the cuvette from the detecting section 14 and sets the cuvette in an installation section (not shown). The liquid in the cuvette set in the installation section is suctioned by a drain nozzle (not shown), and the catcher 18 picks up the reaction container from the installation section and enters the reaction container to the discarding section 17 to perform a discarding process (Step S118). In this manner, the sample analysis ends.

In this manner, the sample analyzer 1 analyzes the sample by transporting one cuvette (sample) by the reaction section 9 and sequentially processes the sample during the transport. In addition, a plurality of samples are sequentially suctioned for each turn and processed in parallel by delaying the analysis (measurement) start timing.

<Primary B/F Separation Process>

Figure 7:
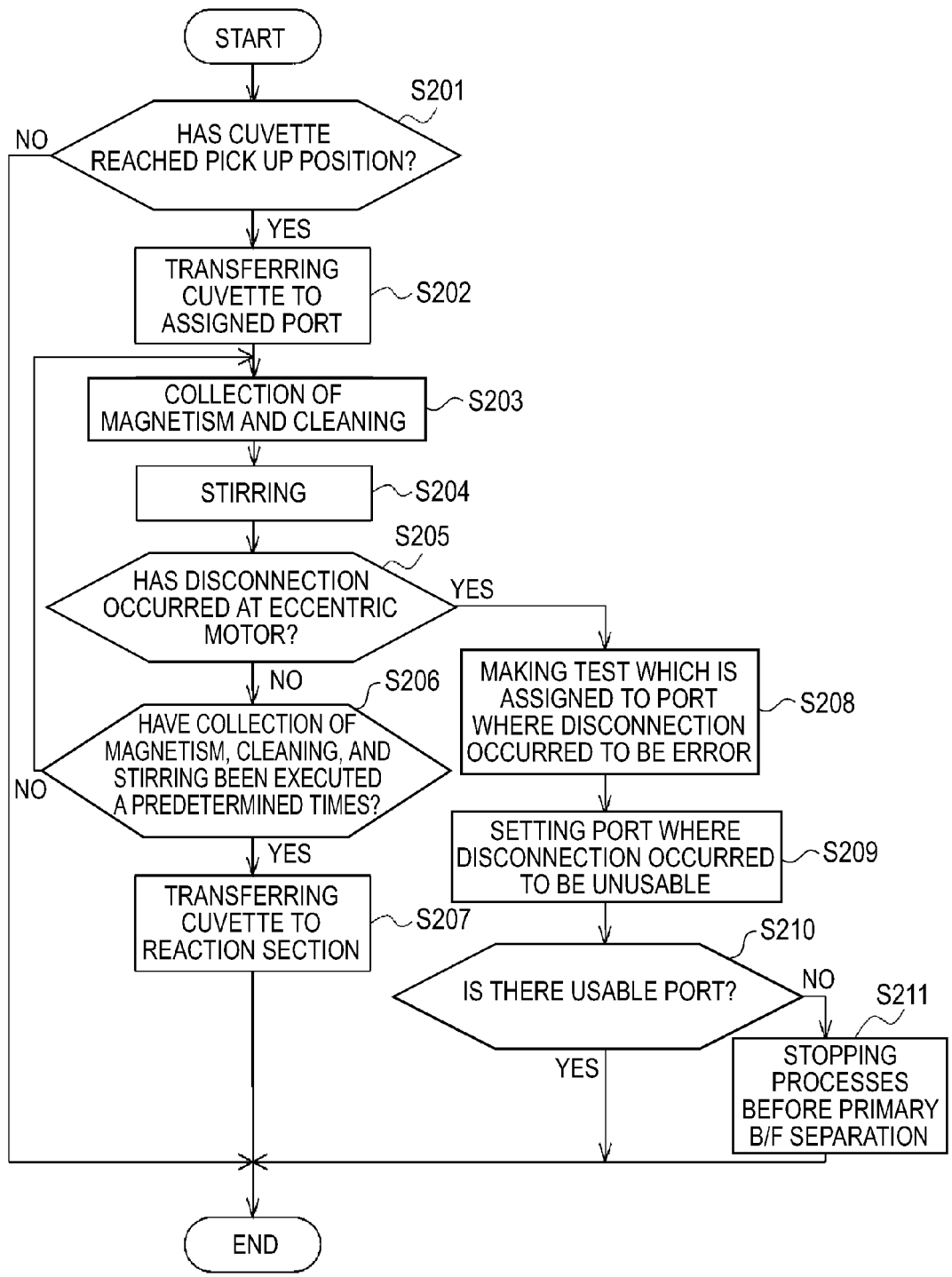
FIG. 7 is a flowchart showing the procedures of a primary B/F separation process.

Next, a process of controlling the primary B/F separating section 11 by the controller 2a (primary B/F separation process) will be described in detail. The CPU 2b of the controller 2a repeatedly executes the primary B/F separation process to be described as follows. FIG. 7 is a flowchart showing the procedures of the primary B/F separation process. In the primary B/F separation process, first, the CPU 2b determines whether a sample (cuvette) which is a target of the primary B/F separation process has reached the pickup position 9A of the reaction section 9 (Step S201). When the sample does not reach the pickup position 9A (NO in Step S201), the CPU 2b ends the process.

In Step S201, when the sample reaches the pickup position 9A (YES in Step S201), the CPU 2b controls the catcher 11b to transfer the cuvette positioned at the pickup position 9A to a port which is assigned in advance in the creation of a schedule to be described later (Step S202). That is, in the schedule the cuvette which is assigned to the first port is transferred to the first port, the cuvette which is assigned to the second port is transferred to the second port, the cuvette which is assigned to the third port is transferred to the third port, and the cuvette which is assigned to the fourth port is transferred to the fourth port.

Next, the CPU 2b moves the holding section 11a in the X1 direction (see FIG. 5) and grips the cuvettes set in the respective ports by the stirring mechanisms 111a, 111b, 111c, and 111d. Then, the CPU 2b lifts the stirring mechanisms 111a, 111b, 111c, and 111d and executes the collection of magnetism of the magnetic particles in the cuvette and the antigen and the capture antibody bound to the magnetic particles, the suction of the unnecessary component, and the cleaning (Step S203). Furthermore, the CPU 2b drives the eccentric motors 112a, 112b, 112c, and 112d to stir the liquid and the magnetic particles in the cuvette (Step S204).

Next, the CPU 2b determines whether disconnection has occurred at any of the eccentric motors 112a, 112b, 112c, and 112d (Step S205). When no disconnection occurs at any of the eccentric motors (NO in Step S205), the CPU 2b determines whether the primary B/F separation operation (the collection of magnetism of the magnetic particles in the cuvette and the antigen and the capture antibody bound to the magnetic particles, the suction of the unnecessary component, the cleaning, and the stirring) has been executed a predetermined number of times (Step S206). When the primary B/F separation operation is not executed the predetermined number of times (NO in Step S206), the process returns to Step S203 and the primary B/F separation operation is executed again. When the primary B/F separation operation is executed the predetermined number of times (YES in Step S206), the CPU 2b controls the catcher 11*b* and transfers the cuvette, which is initially transferred to the holding section 11*a* from the reaction section 9 among the cuvettes held in the holding section 11*a*, to the return position 9B of the reaction section 9 by the catcher 11*b* (Step S207), and ends the process.

On the other hand, when it is determined that disconnection has occurred at any of the eccentric motors 112*a*, 112*b*, 112*c*, and 112*d* in Step S205 (YES in Step S205), the schedule of the cuvette (test) which is assigned to the port where the disconnection of the eccentric motor occurred is made to be an error (Step S208). The CPU 2*b* discards the cuvette which is made to be the error in the schedule without executing the processes (dispensing of reagents, primary B/F separation, secondary B/F separation, detecting process) after it is made to be the error. For example, a cuvette which is made to be an error before reaching the primary B/F separating section passes the pickup position 9A of the primary B/F separating section 11 without being transferred to the primary B/F separating section 11. In addition, at the position at which a reagent is dispensed by the R3 reagent dispensing arm 8, no R3 reagent is dispensed and the cuvette passes the reagent dispensing position. Furthermore, the cuvette passes the pickup position 9C of the secondary B/F separating section 12 without being transferred to the secondary B/F separating section 12. In addition, no R4 reagent and R5 reagent are dispensed and the cuvette passes the respective reagent dispensing positions and reaches a pickup position in the detecting section 14. The cuvette which reaches the pickup position in the detecting section 14 is picked up by the catcher 18 and set in the installation section (not shown) without being transferred to the detecting section 14. The liquid in the cuvette set in the installation section is suctioned by the drain nozzle (not shown). Then, the cuvette is transferred to the discarding section 17 by the catcher 18 to be discarded.

Next, the CPU 2*b* sets the port where the disconnection of the eccentric motor occurred to be unusable (Step S209). This process is performed by storing the information of the unusable port in the RAM 2*d* of the controller 2*a*. Furthermore, the CPU 2*b* determines whether there is a usable port, that is, whether all of the first to fourth ports are unusable (Step S210). When there is a usable port in Step S210 (YES in Step S210), the CPU 2*b* ends the process as is. On the other hand, when there is no usable port (NO in Step S210), the CPU 2*b* stops the processes before the primary B/F separation, that is, the transport of a rack, the supply of a cuvette, the dispensing of an R1 reagent, the dispensing of a sample, the dispensing of an R2 reagent, and the primary B/F separation (Step S211), and ends the process. As a result, even when all of the ports are unusable, the processes after the primary B/F separation, that is, the dispensing of an R3 reagent, the secondary B/F separation process, the dispensing of an R4 reagent and an R5 reagent and the detecting process continue. Accordingly, until it is determined that all of the ports of the primary B/F separating section are unusable, a sample in which the primary B/F separation has ended can be analyzed and the waste of a sample is prevented.

<Creation of Schedule>

Prior to the execution of the sample analysis, a measurement order is registered in the sample analyzer 1. Sample measurement items are designated by this measurement order. In the sample analyzer 1, a measurement order can be registered by a user, and a measurement order can also be received from a server device (not shown). That is, when a user registers a measurement order, the user operates the keyboard 4*c* of the information processing unit 4, and thus the measurement order is input to the sample analyzer 1. When a measurement order is received from a server device, the user registers a measurement order in the server device in advance. In this embodiment, the measurement order means that one or plural measurement items are designated for each of the samples and the sample analyzer 1 is instructed to measure the designated measurement items. Accordingly, one measurement order is input for one sample, and one or plural measurement items are included in one measurement order.

When a measurement order is registered by a user or a server device, the registered measurement order is stored on the hard disk of the information processing unit 4. In addition, the information processing unit 4 transmits the registered measurement order to the measuring unit 2. The CPU 2*b* of the controller 2*a* stores the received measurement order in the RAM 2*d*.

The measurement order can be registered before or after the information processing unit 4 receives a measurement start instruction from a user. When a user gives a measurement start instruction to the information processing unit 4, a command for starting a sample measurement operation is output to the measuring unit 2 from the information processing unit 4. When receiving this command, the CPU 2*b* starts a measurement control process to be described as follows.

Figure 8:
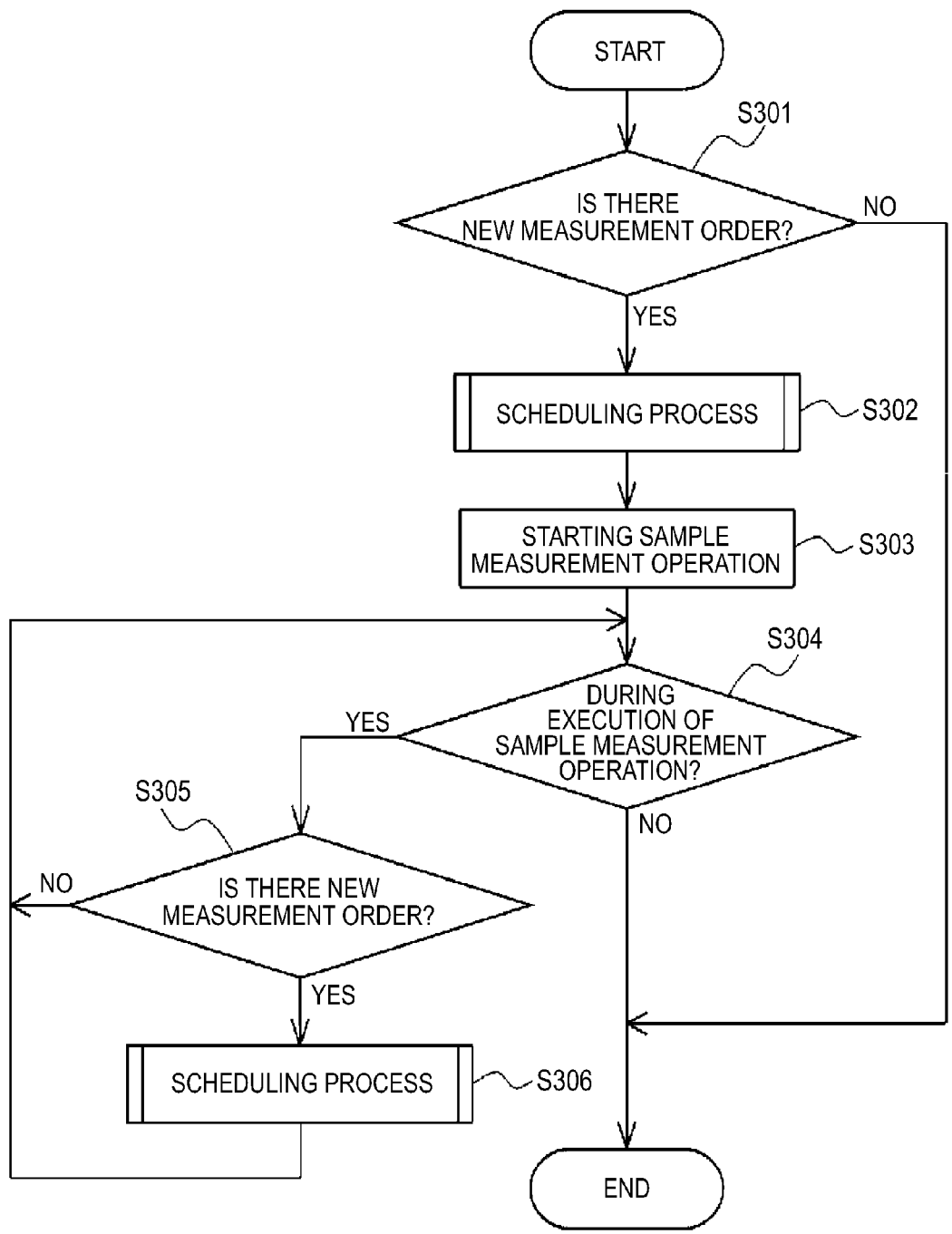
FIG. 8 is a flowchart showing the procedures of a measurement control process.

FIG. 8 is a flowchart showing the procedures of the measurement control process of the controller 2*a*. First, the CPU 2*b* determines whether a measurement order (new measurement order) related to an unexecuted sample measurement is stored in the RAM 2*d* (Step S301). When the new measurement order is not stored in the RAM 2*d* (NO in Step S301), the CPU 2*b* ends the process. On the other hand, when the new measurement order is stored in the RAM 2*d* (YES in Step S301), the CPU 2*b* executes a scheduling process to create a sample measurement schedule (Step S302). The scheduling process will be described later in detail.

Next, the CPU 2*b* controls the mechanisms of the measuring unit 2 and the sample transport unit 3 and starts the sample measurement (Step S303). Accordingly, each sample is measured in accordance with the above-described sample analysis procedures.

The CPU 2*b* determines whether the sample measurement is executed (Step S304). In some cases, a new measurement order is registered during the sample measurement. Accordingly, when the sample measurement is executed (YES in Step S304), the CPU 2*b* determines again whether a new measurement order is stored in the RAM 2*d* (Step S305). When the new measurement order is stored in the RAM 2*d* (YES in Step S305), the CPU 2*b* executes the scheduling process again on the basis of the added new measurement order (Step S306), and returns the process to Step S304. On the other hand, in Step S305, when no new measurement order is stored in the RAM 2*d* (NO in Step S305), the CPU 2*b* returns the process to Step S304 as is. In addition, in Step S304, when the sample measurement is not executed (NO in Step S304), the CPU 2*b* ends the process.

Figure 9:
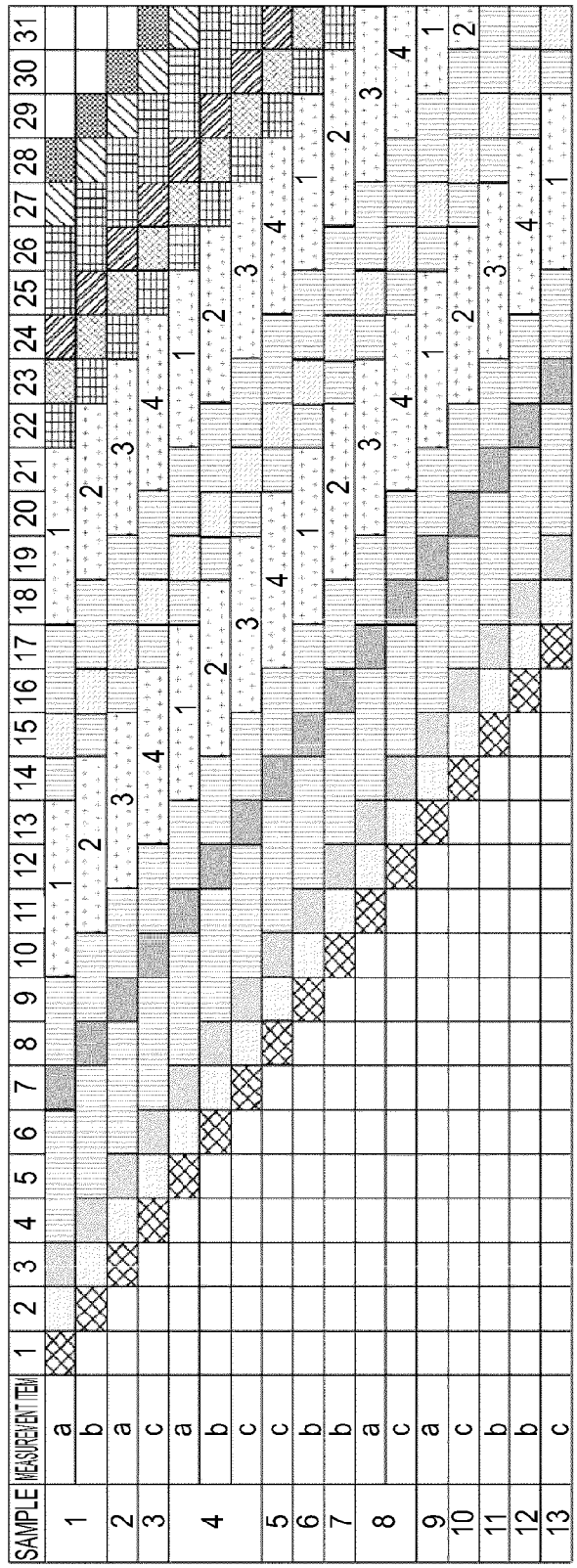
FIG. 9 is a timing chart partially showing an example of a sample measurement schedule.

Next, the creation of a sample measurement schedule will be described in detail. In the scheduling process, a sample measurement schedule is created on the basis of the measurement order. FIG. 9 is a timing chart partially showing an example of a sample measurement schedule. As shown in FIG. 9, the sample measurement schedule is created by assigning operations to be executed for each of continuous turns which are divided at predetermined time intervals (for example, 9 seconds). In the example of FIG. 9, with regard to Sample No. 1, an instruction is made to measure measurement items a and b. In the measurement (test) of the measurement item a in Sample No. 1, the supply of a cuvette in the first turn, the dispensing of an R1 reagent in the second turn, the dispensing of a sample (process of suctioning the sample from a test tube and dispensing the sample in the cuvette) in the third turn, the transport of the cuvette in the fourth to sixth turns, the dispensing of an R2 reagent in the seventh turn, the transport of the cuvette in the eighth and ninth turns, the primary B/F separation in the first port in the 10th to 13th turns, the transport of the cuvette in the 14th turn, the dispensing of an R3 reagent in the 15th turn, the transport of the cuvette in the 16th and 17th turns, the secondary B/F separation in the first port in the 18th to 21st turns, the transport of the cuvette in the 22nd turn, the dispensing of an R4 reagent in the 23rd turn, the dispensing of an R5 reagent in the 24th turn, the transport of the cuvette in the 25th and 26th turns, the photometry (measurement of the antigen amount) in the 27th turn, and the discarding of the cuvette in the 28th turn are planned. In addition, in the test of the measurement item b in Sample No. 1, the supply of a cuvette is planned in the second turn, and subsequently, the same processes as in the test of the measurement item a are continuously planned in the same procedures. That is, with regard to the test of the measurement item b of Sample No. 1, the same schedule as that of the test of the measurement item a is due to be delayed by one turn.

In addition, with regard to Sample No. 2, an instruction is made to measure the measurement a. With regard to Sample No. 3, an instruction is made to test a measurement item c, and with regard to Sample No. 4, an instruction is made to test the measurement items a, b, and c. Similarly, instructions are made to test the measurement item c with regard to Sample No. 5, test the measurement item b with regard to Sample Nos. 6 and 7, test the measurement items a and c with regard to Sample No. 8, test the measurement a with regard to Sample No. 9, test the measurement item c with regard to Sample No. 10, test the measurement item b with regard to Sample Nos. 11 and 12, and test the measurement item c with regard to Sample No. 13. The schedule is created for each test and each of the schedules has the same processes as those in the test of the sample measurement a of Sample No. 1 in the same sequence. In addition, the schedules of these tests are created so that the respective tests are delayed by one turn.

Figure 10:
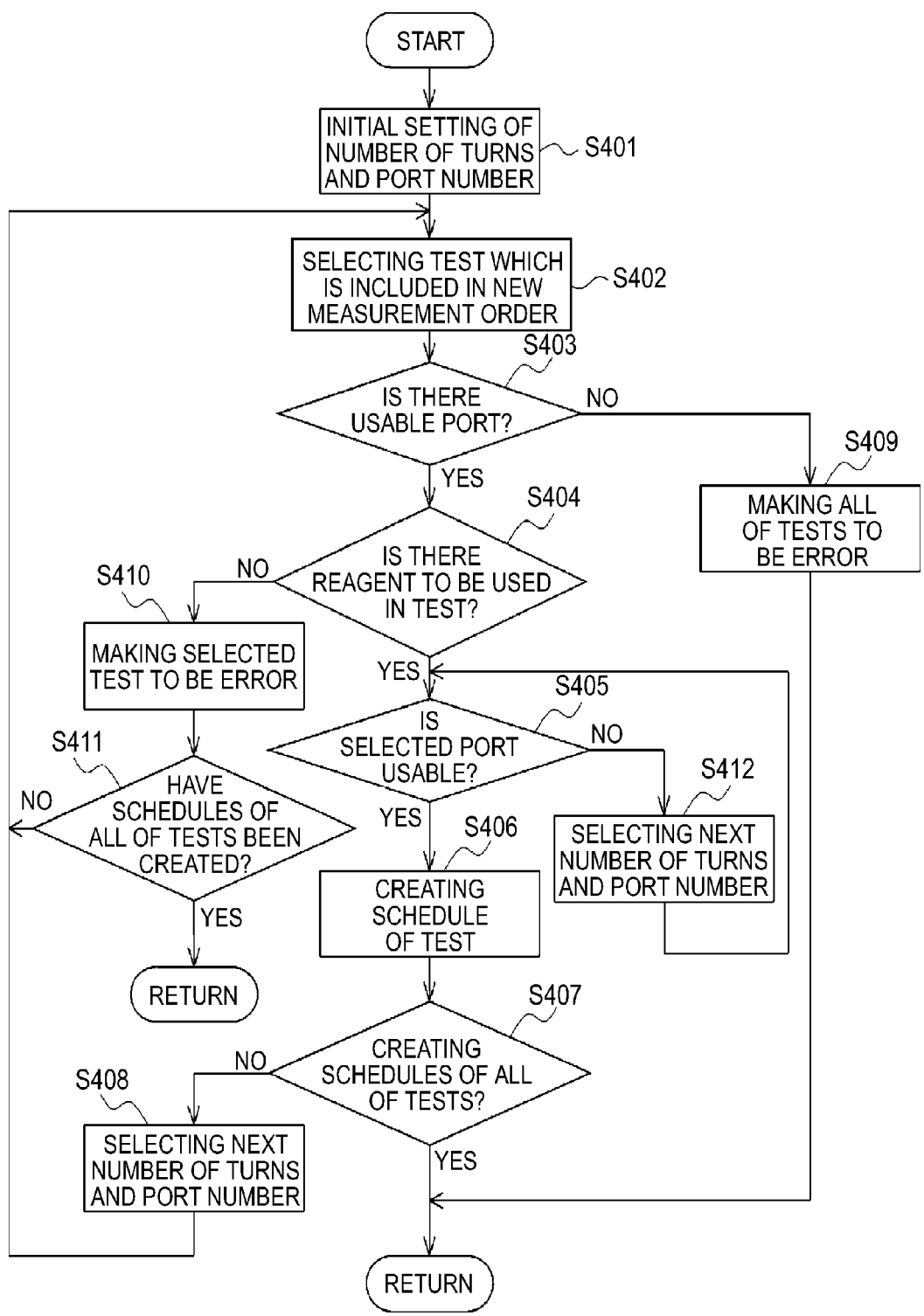
FIG. 10 is a flowchart showing the procedures of a scheduling process.

The scheduling process of creating a schedule of the above-described sample measurement by the controller 2a will be described as follows. FIG. 10 is a flowchart showing the procedures of the scheduling process. In the scheduling process, first, the CPU 2b performs the initial setting of the number of turns and the port number (Step S401). In this process, in the case of an initial scheduling process after the start-up of the measuring unit 2, 1 is set (selected) as the number of turns and 1 is set (selected) as the port number as initial values. In addition, when the second and subsequent scheduling processes are started, the initial values of the number of turns and the port number are not used, but the next number of turns and the next port number of the number of turns and the port number, which are finally selected in the previous scheduling process, are selected. That is, when the number of turns and the port number which are finally selected in the previous scheduling process are "10" and "2", respectively, "11" and "3" are selected as the number of turns and the port number, respectively, in the execution of initial Step S401 of the next scheduling process. In addition, the port number is any one of 1 to 4, and Port Nos. 1 to 4 are repeatedly used. That is, when the port number in the previous scheduling process is "4", the next port number is set to "1".

Next, the CPU 2b selects one, for which the schedule is not created, of the measurement items (test) which are included in the new measurement order stored in the RAM 2d (Step S402).

Next, the CPU 2b determines whether there is at least one usable port with regard to each of the primary B/F separating section 11 and the secondary B/F separating section 12 (that is, whether all of the ports are set to be unusable (Step S403). When there is at least one usable port with regard to each of the primary B/F separating section 11 and the secondary B/F separating section 12 (YES in Step S403), the CPU 2b determines whether there is a reagent to be used in the selected test (Step S404). When there is a reagent to be used in the selected test (YES in Step S404), it is determined whether the port of a selected number is usable (Step S405). When the port of a selected number is usable (YES in Step S405), the CPU 2b creates a schedule of the test so as to start the processes of the test at the selected number of turns, and stores the schedule in the RAM 2d (Step S406).

Next, the CPU 2b determines whether the schedules have been created with regard to all of the tests of the new measurement order stored in the RAM 2d (Step S407). Here, when there is a test of which the schedule is not yet created (NO in Step S407), the CPU 2b selects the next number of turns and the next port number (Step S408), and advances the process to Step S402. On the other hand, when the schedules have been created with regard to all of the tests of the new measurement order (YES in Step S407), the CPU 2b returns the process to the call address of the scheduling process in the main routine (measurement control process). In this manner, the processes of Steps S402 to S408 are repeated and thus the schedule is created as shown in FIG. 9.

In Step S403, when all of the ports are set to be unusable with regard to any of the primary B/F separating section 11 and the secondary B/F separating section 12 (NO in Step S403), the CPU 2b makes all of the tests of the new measurement order be errors (Step S409), and returns the process to the call address of the scheduling process in the main routine (measurement control process). Accordingly, the creation of a new schedule is stopped, and the suction and the dispending of a new sample by the sample dispensing arm are stopped.

In addition, in Step S404, when there is no reagent to be used in the selected test (NO in Step S404), the CPU 2b makes the selected test be an error (Step S410), and determines whether the schedules have been created with regard to all of the tests of the new measurement order stored in the RAM 2d (Step S411). Here, when there is a test of which the schedule is not yet created (NO in Step S411), the CPU 2b advances the process to Step S402 as is. On the other hand, when the schedules have been created with regard to all of the tests of the new measurement order (YES in Step S411), the CPU 2b returns the process to the call address of the scheduling process in the main routine (measurement control process).

In addition, in Step S405, when the port of a selected number is unusable (NO in Step S405), the CPU 2b selects the next number of turns and the next port number (Step S412), and returns the process to Step S405. Accordingly, the ports of the primary B/F separation and the secondary B/F separation are assigned while avoiding the unusable port.

FIG. 11 is a timing chart partially showing another example of the sample measurement schedule. FIG. 11 shows a schedule when the second port of the primary B/F separating section 11 is unusable at the 13th turn in the creation of the schedule shown in FIG. 9. At the time when a problem is detected in the second port of the primary B/F separating section 11, the schedules of the test of the measurement item b of Sample No. 1, the test of the measurement item b of Sample No. 4, and the test of the measurement item b of Sample No. 7 are created already as a schedule with the assigned port number "2". In addition, at the time when the problem is detected, the primary B/F separation is not completed with regard to these all of the tests. Accordingly, the processes to be executed are not executed after the detection of a problem in these tests. The canceled processes are shown in black in the drawing.

In addition, as shown in FIG. 9, when no problem occurs at the second port of the primary B/F separating section 11, a schedule which starts at the turn number "14" is created with regard to the test of the measurement item c of Sample No. 10. However, as shown in FIG. 11, when a problem occurs at the second port of the primary B/F separating section 11, a schedule which is delayed by one turn and starts at the turn number "15" is created with regard to the test of the measurement item c of Sample No. 10, and "3" is assigned as the port number of the primary B/F separating section 11. When the schedule which starts at the turn "14" is made, the primary B/F separation process of this test is started at the turn 23, but none of the remaining ports where no problem occurs are available at the turn 23. Meanwhile, by delaying the turn as described above, the start turn of the primary B/F separation process is the turn 24. At the turn 24, the primary B/F separation process of the third port is completed at the last turn 23, and thus it is possible to start the primary B/F separation process without stopping the cyclic operation of the sample analyzer 1.

Similarly as in the above description, when no problem occurs at the second port of the primary B/F separating section 11, a schedule which is delayed by one turn and starts at the turn number "19" is created, not a schedule which starts at the turn number "18", with respect to a test of the measurement item c with regard to Sample No. 13. In addition, in this schedule, "3" is assigned as the port number of the primary B/F separation section 11.

In this manner, when a problem occurs at the second port of the primary B/F separating section 11, the timing of the sample dispensing is delayed to make a schedule in which the unusable second port is avoided and the port of the primary B/F separating section 11 is assigned, and thus it is possible to continue the measurement of the sample by using the first, third and fourth ports where no problem occurs.

The sample analyzer 1 of this embodiment dispenses a sample in cuvettes at a predetermined cycle, holds the plurality of cuvettes in the reaction section 9, and operates periodically the sections such as the reaction section 9 and the primary B/F separating section 11 to react the sample and reagents for a predetermined reaction time. In the case in which a problem occurs at any of the four ports of the primary B/F separating section 11, when a sample is dispensed at the same cycle as that before the occurrence of the problem, the primary B/F separation process should be performed only with the remaining ports where no problem occurs and there is a shortage of ports to perform the primary B/F separation process of all of the samples, whereby it is necessary to wait for the in-use ports to be available. When waiting for the port to be available, there is a need to stop the cyclic operation of the reaction section 9, and in accordance with the cuvette, the reaction time becomes longer than a predetermined time. In this embodiment, the sample dispensing timing is alternated in order to continue the sample processing by using the remaining ports where no problem occurs, and thus there is no need to wait for the port where no problem occurs to be available and it is possible to continue the sample processing with regard to a cuvette during the reaction in the apparatus without affecting the predetermined reaction time.

In the example shown in FIG. 11, the sample dispensing is paused once at turn 16 and is then performed at the three continuous turns 17 to 19. The sample dispensing is paused again at the turn 20 and is performed at the continuous three turns. In this manner, when a problem occurs at only one of the four ports, a series of operations are repeated in which the sample dispensing is paused for only one turn and is then performed continuously for three turns. Here, when a problem occurs at two ports which are continuously used (ports 1 and 2, ports 2 and 3, ports 3 and 4, or ports 4 and 1) among the four ports, a series of operations are repeated in which the sample dispensing is paused at the continuous two turns and is then performed at the continuous two turns. In this manner, the sample is dispensed for each turn in a state in which no problem occurs, but when a problem occurs at plural ports which are continuously used, the pause of the sample dispensing at the turn number corresponding to the number of the ports where the problem occurred and the sample dispensing at the turn number corresponding to the number of the ports where no problem occurs are repeatedly performed.

As described above, when no problem occurs in any of the ports of the primary B/F separating section 11, the sample dispensing operation which is performed continuously the same four times as the number of the ports is set to one cycle, and this cycle is repeated. When a problem occurs at one port, one operation is paused among the four sample dispensing operations. In addition, when a problem occurs at two ports, two operations are paused among the four sample dispensing operations, and when a problem occurs at three ports, three operations are paused among the four sample dispensing operations. That is, the sample is dispensed four times in one cycle when no problem occurs, and thus when a problem occurs, the operations of the same number as the number of ports where the problem occurred are paused among the four sample dispensing operations of the same number as the number of the ports. In this manner, it is possible to continue the sample processing without affecting the predetermined reaction time.

Although not shown in FIG. 11, the port number 2 of the secondary B/F separating section 12 is used in the secondary B/F separation of Sample No. 11, the port number 3 of the secondary B/F separating section 12 is used in the secondary B/F separation of Sample No. 12, and the port number 4 of the secondary B/F separating section 12 is used in the secondary B/F separation of Sample No. 13. That is, with regard to a test in which the port number of the secondary B/F separating section 12 is already assigned at the time of the occurrence of a problem at the turn 13, the port number which is already assigned is used to continue the measurement. With regard to a test in which the port number of the secondary B/F separating section 12 is assigned after the occurrence of a problem at the turn 13, there is no need for the port number of the secondary B/F separating section 12 to be assigned corresponding to the port number of the primary B/F separating section 11, and thus with regard to these tests, the port number of the secondary B/F separating section 12 is sequentially assigned among 1 to 4.

Due to the above-described configuration, the invention is advantageous in the following case. Assuming that a problem occurs at the port number 2 of the primary B/F separating section 11 and a problem occurs at the port number 3 of the secondary B/F separating section 12, when it is necessary to assign the same port number to the respective primary B/F separating section 11 and secondary B/F separating section 12, only two combinations, that is a combination of the port number 1 of the primary B/F separating section 11 and the port number 1 of the secondary B/F separating section 12 and a combination of the port number 4 of the primary B/F separating section 11 and the port number 4 of the secondary B/F separating section 12 remain. That is, the port number 3 of the primary B/F separating section 11 and the port number 2 of the secondary B/F separating section 12 are not used even when no problem occurs therein. Accordingly, the processing performance of each of the B/F separating sections is reduced to only ¾, but the entire processing performance is reduced to ½. Meanwhile, when it is permitted to assign different port numbers to the respective primary B/F separating section 11 and secondary B/F separating section 12, it is possible to use all of the three ports, where no problem occurs, of the B/F separating sections. As a result, the processing performance can be kept to ¾ and a reduction in the processing performance can be minimized.

Due to the above-described configuration, even when a problem occurs at any stirring mechanism of the primary B/F separating section 11 and the secondary B/F separating section 12, a mixture in a reaction container can be stirred by using a stirring mechanism other than the stirring mechanism where the problem occurred. Accordingly, even after the occurrence of the above-described problem, a new sample can be dispensed and the sample can be continuously analyzed. In addition, due to the configuration in which with regard to the respective ports, the same B/F separation process is executed by being delayed by one turn in the primary B/F separating section 11 and the secondary B/F separating section 12, the controller 2a may execute a control program for executing the B/F separation process by being delayed by one turn with regard to the respective ports, and the structure of the control program for the primary B/F separating section 11 and the secondary B/F separating section 12 can be simplified. Furthermore, in the case in which any port of the primary B/F separating section 11 or the secondary B/F separating section 12 is made to be unusable due to a problem, two turns are simply delayed and the above-described control program is executed when avoiding the unusable port, whereby there is no need to separately provide a control program for when a problem occurs, and the program development man-hours and costs can be suppressed. Furthermore, according to the above-described configuration, a cuvette other than a cuvette which is due to be processed in a stirring mechanism where a problem occurred among cuvettes disposed at the upper stream side than the B/F separating section where a problem occurred can be stirred in accordance with the plan, and thus the measurement can be continued. Accordingly, in comparison to the conventional technique in which all of cuvettes disposed at the upper stream side than the B/F separating section where a problem occurred are discarded, a waste of sample and reagent when a problem occurs at the B/F separating section can be significantly reduced.

(Other Embodiments)

In the above-described embodiments, the configuration has been described in which the controller 2a of the measuring unit 2 controls the mechanisms in the measuring unit 2, but the invention is not limited thereto. A configuration may be provided in which the information processing unit 4 of the sample analyzer 1 may perform a process of controlling the above-described mechanisms.

In addition, in the above-described embodiments, the configuration has been described in which when a problem occurs at a port of the primary B/F separating section 11 or the secondary B/F separating section 12, the processing steps to be executed after the occurrence of the problem are stopped with regard to a test having a schedule in which the port is already assigned at the time of the detection of the problem, but the invention is not limited thereto. A configuration may be provided in which when a problem is detected, schedules are created again so as not to use a port where the problem occurred with regard to a plurality of tests including a test having a schedule in which the port is already assigned, and the sample measurement is executed according to the newly created schedules.

In addition, in the above-described embodiments, the configuration has been described in which in the primary B/F separating section 11 (secondary B/F separating section 12), the plurality of stirring mechanisms 111a, 111b, 111c, and 111d performing the same process (stirring) are provided to execute a stirring process by the stirring mechanisms where no problem occurs when a problem occurs at some of the stirring mechanisms, but the invention is not limited thereto. A configuration may be provided in which when mechanisms other than the stirring mechanisms, for example, a plurality of R1 reagent dispensing arms are provided and no problem occurs in any of the R1 reagent dispensing arms, a process of dispensing an R1 reagent in one cuvette by one R1 reagent dispensing arm and a process of dispensing an R1 reagent in another cuvette by another R1 reagent dispensing arm are executed in a duplicate manner, and when a problem occurs at one R1 reagent dispensing arm, another dispensing arm executes the subsequent R1 reagent dispensing process.

In addition, in the above-described embodiments, the configuration has been shown in which a cuvette in which an R1 reagent and a sample are dispensed is transferred to the reaction section, but the invention is not limited thereto. For example, a configuration may be provided in which an empty cuvette is set in the reaction section and an R1 reagent and a sample are dispensed therein.

In addition, in the above-described embodiments, the configuration has been described in which the sample analyzer 1 is set as an immunoassay apparatus, but the invention is not limited thereto. The sample analyzer may be set as a sample analyzer other than an immunoassay apparatus, such as a blood cell counter, a blood coagulation measuring apparatus, a biochemical analyzer, an in-urine physical component analyzer or a urine qualitative analyzer. However, the sample analyzer is preferably set as a biochemical analyzer or a blood coagulation measuring apparatus which is a sample analyzer having a configuration in which a cuvette is transported by a transporter having a rotation table shape and processes such as the dispensing of a sample and the dispensing of a reagent are executed at a plurality of places on a path on which transporting is carried out by the transporter.

In addition, in the above-described embodiments, the example has been shown in which the R2 reagent dispensing arm 7 has a function of dispensing an R2 reagent and the R3 reagent dispensing arm has a function of dispensing an R3 reagent. However, one multifunctional unit having a function of dispensing an R2 reagent and an R3 reagent may be provided.

What is claimed is:

1. A sample analyzer comprising:
    a sample dispenser configured to dispense a sample into a reaction container;
    a sample transporter configured to sequentially transport a plurality of samples along a transporting path;
    a first processing station configured to perform a separating operation in which a target analyte in the sample is separated from other spurious contents in the reaction container, wherein the first processing station including (a) a first plurality of ports each configured to receive a sample and execute the separating operation on the received sample, the first plurality of ports being each identifiable by an incremental number, and (b) a first transferring section configured to load and unload the sample between the sample transporter and one of the ports in the first processing station;
    a measuring section configured to analyze the separated target analyte in the sample; and a controller programmed to execute sample processing operations on each of the plurality of samples sequentially at successive regular time intervals each represented by an operation count incremental at the regular time interval, the sample processing operations including:
- (i) dispensing, by the sample dispenser, one of the plurality of samples into the reaction container;
- (ii) transporting, by the sample transporter, the dispensed sample to the processing station along the transporting path;
- (iii) loading, by the first transferring section, the transported sample from the sample transporter onto one of the ports in the first processing station;
- (iv) separating the target analyte in the loaded sample at the one port in the first processing station;
- (v) unloading, by the transferring section, the separated target analyte from the one port in the first processing station onto the sample transporter after completing the separating operation on the sample at the one port in the first processing station;
- (vi) transporting, by the sample transporter, with the separated target analyte to the measuring section along the transporting path; and
- (vii) analyzing the separated target analyte by the measuring section, wherein the controller is further programmed to:

for each of the plurality of samples, execute scheduling of the sample processing operations in which the controller generates incremental start counts and incremental first port identification numbers in pairs and assigns the pairs of generated start counts and first port identification numbers sequentially to each of the plurality of samples so that each sample in the plurality of samples has a start count and a first port identification number both incremental from one sample to a next sample;

proceed with the sample processing operations on a sample in the plurality of samples from a count of the operation count equal to the start count assigned to the sample, wherein the sample processing operations for the sample advance, starting from the start count assigned to the sample, from one operation to a next operation in synchronism with an increment of the operation count, and at a scheduled count of the operation count incremented from the start count assigned to the sample, the sample is delivered to one of the ports in the first processing station identified by the first port identification number assigned to the sample;

determine whether a trouble has occurred with respect to any one of the ports in the first processing station;

in response to a determination that a trouble has occurred with respect to one of the ports in the first processing station, modify the scheduling of the sample processing operations for the plurality of samples yet to proceed with the sample processing operations such that if the first port identification number generated for one of the samples in the plurality of samples yet to be processed identifies the troubled port in the first processing station, increment the start count and first port identification number generated in pair for the sample with the identified trouble port in the first processing station and all subsequent samples in the plurality of samples and assign the incremented start count and incremented first port identification number to the sample with the identified trouble port in the first processing station and all subsequent samples in the plurality of samples; and continue to proceed with the sample processing operations on the remaining samples in the plurality of samples by starting the sample processing operation on each of the remaining samples, including determining whether a trouble has occurred with respect to any one of the ports in the first processing station, when the operation count is equal to the start count assigned to each sample, wherein the sample processing operations for the sample advance, starting from the start count assigned to the sample, from one operation to a next operation in synchronism with an increment of the operation count, and at a scheduled count of the operation count incremented from the start count assigned to the sample, the sample is delivered to one of the ports in the first processing station identified by the first port identification number assigned to the sample.

2. The sample analyzer according to claim 1, wherein if a number of the ports in the first processing station is equal to n, and if a number of troubled ports in the first processing station is equal to m, an operation rate of the sample analyzer is represented by (n−m)/n.

3. The sample analyzer according to claim 1, further comprising a first reagent dispenser configured to dispense a reagent in a reaction container that has already been dispensed with a sample and is being transported to the first processing station.

4. The sample analyzer according to claim 3, further comprising a second reagent dispenser configured to dispense a second reagent in a reaction container that is unloaded from the first processing station to the sample transporter.

5. The sample analyzer according to claim 1, wherein it is determined, when some of the sample processing operations are already performed on a sample, that a trouble has occurred with respect to one of the ports in the first processing station, the controller is programmed to cancel a reminder of the sample processing operations to be performed on the sample and operate the sample transporter to transport the sample through an end of the transporting path.

6. The sample analyzer according to claim 1, wherein the sample transporter includes a rotation table configured to hold a plurality of the samples in a circular manner, and the rotation table rotates to transport the samples.

7. The sample analyzer according to claim 1, further comprising:
- a container supply section configured to sequentially supply the reaction containers to the sample dispenser; and
- a catcher configured to set one reaction container at a time containing a sample dispensed therein to the sample transporter.

8. The sample analyzer according to claim 7, further comprising a third reagent dispenser configured to dispense a third reagent in the reaction container that is supplied by the container supply section.

9. The sample analyzer according to claim 1, wherein when a trouble occurs with respect to all of the ports in the first processing station, the controller is programmed to stop the sample dispenser from dispensing a sample.

10. The sample analyzer according to claim 1, further comprising a second processing station configured to perform a separating operation in which a target analyte in the sample is separated from other spurious contents in the reaction container, wherein the second processing station including (a) a second plurality of ports each configured to receive the sample and execute the separating operation on the received sample, the ports being each identifiable by an incremental number, and (b) a second transferring section configured to load and unload the sample between the sample transporter and one of the ports in the second processing station
wherein the sample processing operation further comprises:
(viii) transporting, by the sample transporter, the sample to the second processing station along the transporting path;
(ix) loading, by the second transferring section, the transported sample from the sample transporter onto one of the ports in the second processing station;
(x) separating the target analyte in the loaded sample at the one port in the second processing station; and
(xi) unloading, by the second transferring section, the separated target analyte from the one port in the second processing station onto the sample transporter after completing the separation operation on the sample at the one port in the second processing station.

11. The sample analyzer according to claim 1, wherein the separating operation by the first processing station includes a B/F separation operation to remove free antigens included in the sample.

12. The sample analyzer according to claim 1, wherein the first processing station further comprises:
a plurality of stirring mechanisms provided in association with the ports in the first processing station and configured to stir the samples received in the ports in the first processing station; and
a plurality of disconnection detecting circuits provided, respectively, to the ports in the first processing station and configured to detect a problem with respect to any of the stirring mechanisms.

13. The sample analyzer according to claim 12, wherein each of the stirring mechanisms has a motor for vibrating the reaction container, and each of the disconnection detecting circuits detects a trouble of the motor of the corresponding stirring mechanism.

14. The sample analyzer according to claim 12, wherein the stirring mechanisms are fixed to a structure, and
the first processing station is configured to move the structure to lift the samples in the ports in the first processing station and operate the stirring mechanisms to stir the lifted samples.

15. A sample analyzer comprising:
a sample dispenser configured to dispense a sample into a reaction container;
a sample transporter configured to sequentially transport a plurality of samples along a transporting path;
a first processing station configured to perform a separating operation in which a target analyte in the sample is separated from other spurious contents in the reaction container, wherein the first processing station including (a) a first plurality of ports each configured to receive a sample and execute the separating operation on the received sample, the first plurality of ports being each identifiable by an incremental number, and (b) a first transferring section configured to load and unload the sample between the sample transporter and one in the ports in the first processing station;
a second processing station configured to perform a separating operation in which a target analyte in the sample is separated from other spurious contents in the reaction container, wherein the second processing station including (a) a second plurality of ports each configured to receive the sample and execute the separating operation on the received sample, the ports being each identifiable by an incremental number, and (b) a second transferring section configured to load and unload the sample between the sample transporter and one of the ports in the second processing station
a measuring section configured to analyze the separated target analyte in the sample; and
a controller programmed to execute sample processing operations on each of the plurality of samples sequentially at successive regular time intervals each represented by an operation count incremental at the regular time interval, the sample processing operations including:
(i) dispensing, by the sample dispenser, one of the plurality of samples into the reaction container;
(ii) transporting, by the sample transporter, the dispensed sample to the processing station along the transporting path;
(iii) loading, by the first transferring section, the transported sample from the sample transporter onto one of the ports in the first processing station;
(iv) separating the target analyte in the loaded sample at the one port in the first processing station;
(v) unloading, by the transferring section, the separated target analyte from the one port in the first processing station onto the sample transporter after completing the separating operation on the sample at the one port in the first processing station;
(vi) transporting, by the sample transporter, with the separated target analyte to the measuring section along the transporting path; and
(vii) analyzing the separated target analyte by the measuring section,
(viii) transporting, by the sample transporter, the sample to the second processing station along the transporting path;
(ix) loading, by the second transferring section, the transported sample from the sample transporter onto one of the ports in the second processing station;
(x) separating the target analyte in the loaded sample at the one port in the second processing station; and
(xi) unloading, by the second transferring section, the separated target analyte from the one port in the second processing station onto the sample transporter after completing the separation operation on the sample at the one port in the second processing station,
wherein the controller is further programmed to:
for each of the plurality of samples, execute scheduling of the sample processing operations in which the controller generates incremental start counts, incremental first port identification numbers and incremental second port identification numbers in a set and assigns the sets of generated start counts, first port identification numbers and second port identification numbers sequentially to each of the plurality of samples so that each sample in the plurality of samples has a start count and first and second port identification numbers all incremental from one sample to a next sample;
proceed the sample processing operations on a sample in the plurality of samples from a count of the operation count equal to the start count assigned to the sample, wherein the sample processing operations for the sample advance, starting from the start count assigned to the sample, from one operation to a next operation in synchronism with an increment of the operation count, and at a scheduled count of the operation count incremented from the start count assigned to the sample, the sample is delivered to one of the ports in the first processing station identified by the first port identification number assigned to the sample and to one of the ports in the second processing station identified by the second port identification number assigned to the sample;

determine whether a trouble has occurred with respect to any one of the ports in the first processing station;

in response to a determination that a trouble has occurred with respect to one of the ports in the first processing station, modify the scheduling of the sample processing operations for the plurality of samples yet to proceed with the sample processing operations such that if the first port identification number generated for one of the samples yet to be processed in the plurality of samples identifies the troubled port in the first processing station, increment the start count and first port identification number generated in pair for the sample with the identified trouble port in the first processing station and all subsequent samples in the plurality of samples and assign the incremented start count and incremented first port identification number to the sample with the identified trouble port in the first processing station and all subsequent samples in the plurality of samples;

determine whether a trouble has occurred with respect to any one of the ports in the second processing station;

in response to a determination that a trouble has occurred with respect to one of the ports in the second processing station, modify the scheduling of the sample processing operations for the plurality of samples yet to proceed with the sample processing operations such that if the second port identification number generated for one of the samples in the plurality of samples yet to be processed identifies the troubled port in the second processing station, increment the start count, first port identification number and second port identification number generated in a set for the sample with the identified trouble port in the second processing station and all subsequent samples in the plurality of samples and assign the incremented start count, incremented first port identification number and incremented second port identification number to the sample with the identified trouble port and all subsequent samples in the plurality of samples; and continue to proceed with the sample processing operations on the remaining samples in the plurality of samples from a count of the operation count equal to the start count assigned to the sample, including determining whether a trouble has occurred with respect to any one of the ports in the first or second processing station, wherein the sample processing operations for the sample advance, starting from the start count assigned to the sample, from one operation to a next operation in synchronism with an increment of the operation count, and at a scheduled count of the operation count incremented from the start count assigned to the sample, the sample is delivered to one of the ports in the first processing station identified by the first port identification number assigned to the sample and to one of the ports in the second processing station identified by the second port identification number assigned to the sample.

* * * * *